United States Patent [19]

Gutman

[11] 4,327,218

[45] Apr. 27, 1982

[54] N-ARYL, 2-PHENOXY NICOTINAMIDE COMPOUNDS AND THE HERBICIDAL USE THEREOF

[75] Inventor: Arnold D. Gutman, Berkeley, Calif.

[73] Assignee: Stauffer Chemical Company, Westport, Conn.

[21] Appl. No.: 210,990

[22] Filed: Nov. 28, 1980

Related U.S. Application Data

[62] Division of Ser. No. 80,971, Oct. 1, 1979, Pat. No. 4,270,946.

[51] Int. Cl.³ .................................. C07D 213/64
[52] U.S. Cl. ......................................... 546/291
[58] Field of Search ..................... 546/291; 424/266

[56] References Cited

U.S. PATENT DOCUMENTS

| | | | |
|---|---|---|---|
| 3,822,278 | 7/1974 | DuFour | 424/266 X |
| 3,876,648 | 4/1975 | Haas et al. | 424/266 X |
| 3,984,423 | 10/1976 | Chimeno | 424/266 X |
| 4,115,102 | 9/1978 | Takahashi | 71/94 |
| 4,131,744 | 12/1978 | Sundeen et al. | 424/266 X |
| 4,179,509 | 12/1979 | Schwender | 424/266 |

FOREIGN PATENT DOCUMENTS

| | | |
|---|---|---|
| 3890 | 9/1979 | European Pat. Off. . |
| 2140772 | 1/1973 | France . |

*Primary Examiner*—Catherine L. Mills
*Attorney, Agent, or Firm*—Joel G. Ackerman

[57] ABSTRACT

New compounds having the formula

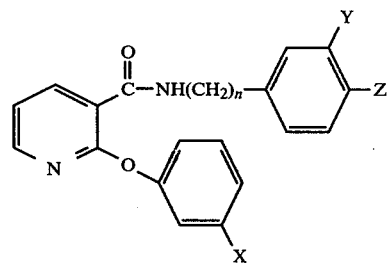

in which n is 0 or 1; X is halogen, $C_1$–$C_3$ alkyl, trifluoromethyl or carboethoxy; Y and Z are independently hydrogen, lower alkyl, halo-lower alkyl, thio(halo-lower alkyl), lower alkoxy, nitro, cyano or halogen; provided that:
 if X is carboethoxy, Z in halogen and Y is hydrogen or halogen; and
 if Y and Z are both halogen, X is halogen, trifluoromethyl or carboethoxy.

These compounds have been found to exhibit herbicidal properties.

52 Claims, No Drawings

N-ARYL, 2-PHENOXY NICOTINAMIDE COMPOUNDS AND THE HERBICIDAL USE THEREOF

This is a division of application Ser. No. 080,971, filed Oct. 1, 1979, now U.S. Pat. No. 4,270,946.

This invention relates to novel herbicidal compounds having the formula

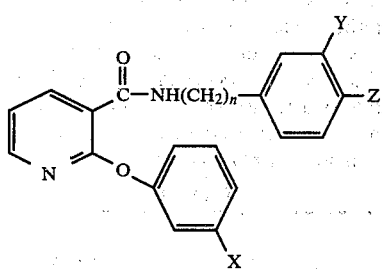

in which n is 0 or 1; X is halogen, $C_1$–$C_3$ alkyl, trifluoromethyl or carboethoxy; Y and Z are independently hydrogen, lower alkyl, halo-lower alkyl, thio(halo-lower alkyl), lower alkoxy, nitro, cyano or halogen; provided that:
  if X is carboethoxy, Y is hydrogen and Z is hydrogen or halogen; and
  if Y and Z are both halogen, X is halogen, trifluoromethyl or carboethoxy.

These compounds have been found to exhibit herbicidal properties.

The term "halogen" or "halo" includes fluoro, chloro, bromo and iodo. The term "lower alkoxy" is meant to include such groups having from 1 to 4 carbon atoms, one example being methoxy. The term "halo-lower alkyl" is meant to include such groups having from 1 to 4 carbon atoms and from 1 to 4 halogen atoms, which may be of the same or different types. A particularly preferred member of this group is trifluoromethyl. The term "thio(halo-lower alkyl)" is meant to include groups as defined under the term "halo-alkyl", additionally possessing a sulfur atom. A particularly preferred member of this group is trifluoromethylthio.

The compounds of this invention have been found to be active herbicides; that is, the compounds have been found herbicidally active against various species of weeds. In the broadest sense, the term "weeds" refer to plants which grow in locations in which they are not desired. As will be seen from the data which follows, these compounds show various activities as pre-emergence and/or post-emergence herbicides. In some cases they show particular activity against various weed species. In addition, many compounds have been found to show selective herbicidal activity controlling certain weeds in the presence of certain crops, particularly wheat.

This invention therefore, also relates to a method for controlling undesirable vegetation comprising applying to such vegetation a herbicidally effective amount of a compound as described herein, and also relates to herbicidal compositions of matter comprising a herbicidally effective amount of a compound as described herein plus an inert diluent or carrier suitable for use with herbicides. In addition, this invention also relates to a method for selectively controlling undesirable vegetation in the presence of a crop, particularly wheat, comprising applying to the locus where control is desired, either prior or subsequent to the emergence of vegetation, a selectively herbicidally effective amount of a compound as described herein (the amount being sufficient to control undesirable vegetation but being substantially non-injurious to wheat) and also relates to selective herbicidal compositions of matter comprising a herbicidally effective amount of such a compound.

As used herein, the term "herbicide" means a compound which controls or modifies the growth of plants, particularly undesirable plants. By the term "herbicidally effective amount" is meant an amount of compound which causes controlling or modifying effect on the growth of plants. The term "plants" is meant to include germinant seeds, emerging seedlings and established vegetation including roots and above ground portion. Such modifying and controlling effects include all deviations from natural development.

In general, the compounds of the present invention can be prepared by reaction of the appropriate 2-(3-substituted phenoxy)nicotinoyl chloride with an aniline or benzyl amine;

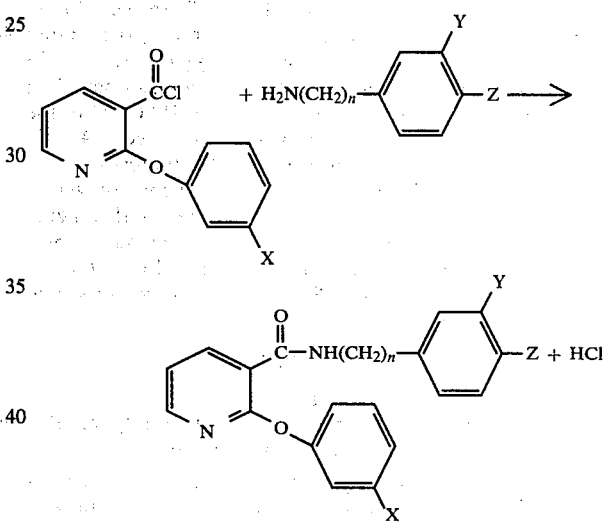

in which X, Y, Z and n are as previously defined. The reaction is carried out in the presence of an acid acceptor such as caustic, an additional equivalent of the reacting amine, or another amine (triethylamine is preferred). Reaction temperatures may range from about 0° to about 110° C. at atmospheric pressure. Any of a number of solvents may be used, for instance, methylene chloride, diethyl ether, benzene and, preferably, toluene. The product may be recovered by first removing the byproduct salt or amine salt with water, then recovering the product from the organic layer by conventional means.

The nicotinoyl chlorides are prepared from the corresponding carboxylic acids by the conventional technique of reacting the acid with a suitable chlorinating agent such as phosgene, $PCl_3$, $PCl_5$, or, preferably thionyl chloride. Temperatures range from about 25° to about 110° C. Solvents such as those mentioned above may be used. The acids may be prepared by reacting a meta-substituted phenol with 2-chloronicotinic acid, as described by Villani, et al., J. Medicinal Chemistry 18, 1 (1975).

The following are examples of the preparation of representative compounds according to the present invention:

EXAMPLE 1

Preparation of 2-(3-trifluoromethylphenoxy)N-(3-nitrophenyl)-nicotinamide (Compound 3)

(a) There were combined 14.1 grams (0.05 mole) 2-(3-trifluoromethylphenoxy)nicotinic acid, 0.1 grams triethylamine hydrochloride and 150 milliliters of chloroform. The mixture was stirred and heated to reflux. Then, 6.5 grams (0.055 mole) thionyl chloride was slowly added. After addition was complete the reaction mass was heated under reflux until hydrogen chloride evolution had ceased (about 30 minutes); it was then cooled to room temperature, filtered, and the solvent removed under vacuum producing 10.0 grams (66.7% of theoretical yield) of 2-(3-trifluoromethylphenoxy)-nicotinoyl chloride. The structure was confirmed by infrared spectral analysis.

(b) A solution of 1.5 grams (0.011 mole) 3-nitroaniline and 1.0 gram (0.011 mole) triethylamine in 100 milliliters toluene was placed in a flask. There was slowly added, with stirring, a solution of 3.2 grams (0.011 mole) 2-(3-trifluoromethylphenoxy)nicotinoyl chloride in 25 milliliters toluene. The rate of addition was controlled so as to maintain the temperature below 35° C. After the addition was complete the mixture was stirred at 45° C., for one hour, cooled, poured into 100 milliliters toluene, and washed with two 150-milliliter portions of water. The organic phase was separated, dried with magnesium sulfate, filtered and the solvent removed to produce 3.3 grams (73.3% of theoretical yield) of the desired product, m.p. 90°-95° C. The structure was confirmed by mass spectrometry.

EXAMPLE 2

Preparation of 2(3-trifluoromethyphenoxy)N-(3,4-dimethylphenyl)-nicotinamide (Compound 10)

In the same manner as in Example 1, 0.3 grams (0.01 mole) 2(3-trifluoromethylphenoxy)nicotinoyl chloride 1.2-grams (0.01 mole) 3,4-dimethylaniline, 1.0 grams (0.01 mole) triethylamine and 125 milliliters toluene were combined to yield 2.3 grams (59.6% of theoretical yield) of the desired product, $n_D^{30}$ 1.5345. The structure was confirmed by mass spectrometry.

EXAMPLE 3

Preparation of 2(3-trifluoromethylphenoxy)N-(3,4-dichlorophenyl)-nicotinamide (Compound 12)

In the manner as in Example 1, 2.75 grams (0.009 mole) of 2(3-trifluoromethyphenoxy)nicotinoyl chloride, 1.5 grams (0.009 mole) 3,4-dichloroaniline, 0.9 grams (0.009 mole) triethylamine and 125 milliliters toluene were combined to yield 2.3 grams (59.8% of theoretical yield) of the desired product, a waxy solid. The structure was confirmed by mass spectrometry.

EXAMPLE 4

Preparation of 2-(3-chlorophenoxy)N-(4-methylphenyl)nicotinamide (Compound 25)

(a) In the same manner as in Example 1(a), 22.1 grams 2(3-chlorophenoxy)nicotinic acid, 13.0 grams (0.1 mole) thionyl chloride, 0.5 grams triethylamine hydrochloride and 200 milliliters chloroform were combined to yield 23.2 grams (98.3% of theoretical) of 2(3-chlorophenoxy)nicotinoyl chloride, m.p. 72°-74° C. The structure was confirmed by mass spectrometry.

(b) In the same manner as in Example 1(b), 1.1 grams (0.01 mole) 2(3-chlorophenoxy)nicotinoyl chloride, 1.0 grams (0.01 mole) 4-methylaniline, 1.0 grams (0.01 mole) triethylamine and 125 milliliters toluene were combined to yield 2.4 grams (70.9% of theoretical yield) of the desired product, m.p. 140°-143° C. The structure was confirmed by mass spectrometry.

Table 1 which follows contains a list of representative compounds of the present invention. Structures of all compounds were confirmed by infrared nuclear magnetic resonance and/or mass spectrometric analyses.

TABLE 1

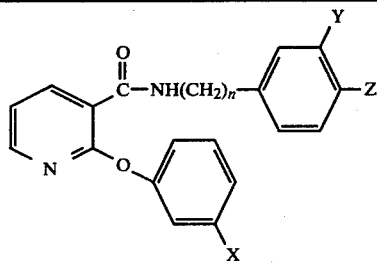

| Compound No. | X | Y | Z | n | m.p., °C., or $n_D^{30}$ |
|---|---|---|---|---|---|
| 1 | CF3 | CF3 | H | 0 | 86–90 |
| 2 | CF3 | SCF3 | H | 0 | 1.5250 |
| 3 | CF3 | NO2 | H | 0 | 90–95 |
| 4 | Cl | CF3 | Cl | 0 | 105–108 |
| 5 | Cl | Cl | Cl | 0 | 146–149 |
| 6 | Cl | SCF3 | H | 0 | 98–100 |
| 7 | Cl | NO2 | H | 0 | 160–162 |
| 8 | Cl | CH3 | CH3 | 0 | 132–135 |
| 9 | CF3 | CF3 | Cl | 0 | 1.5073 |
| 10 | CF3 | CH3 | CH3 | 0 | 1.5345 |
| 11 | CF3 | H | Cl | 0 | 1.5573 |
| 12 | CF3 | Cl | Cl | 0 | (waxy solid) |
| 13 | CF3 | Cl | H | 0 | 122–124 |
| 14 | CF3 | H | Br | 0 | 130–132 |
| 15 | CF3 | H | H | 0 | 158–160 |
| 16 | CF3 | H | CH3 | 0 | 161–163 |
| 17 | CF3 | H | CN | 0 | 140–145 |
| 18 | CF3 | H | OCH3 | 0 | 138–140 |
| 19 | CF3 | H | NO2 | 0 | (waxy solid) |
| 20 | CF3 | CH3 | H | 0 | 118–119 |
| 21 | COOC2H5 | H | Cl | 0 | 114–116 |
| 22 | COOC2H5 | Cl | Cl | 0 | 147–149 |
| 23 | Cl | H | Cl | 0 | 122–124 |
| 24 | Cl | H | H | 0 | 115–117 |
| 25 | Cl | H | CH3 | 0 | 140–143 |
| 26 | Cl | Cl | H | 0 | 113–115 |
| 27 | Cl | CF3 | H | 0 | 99–102 |
| 28 | Cl | H | OCH3 | 0 | 108–110 |
| 29 | Cl | H | Br | 0 | 126–128 |
| 30 | CH3 | H | H | 0 | 127–128 |
| 31 | CH3 | Cl | H | 0 | 93–95 |
| 32 | CH3 | H | CH3 | 0 | 148–149 |
| 33 | Cl | CH3 | H | 0 | 134–136 |
| 34 | Cl | H | H | 1 | 66–68 |
| 35 | Cl | OCH3 | H | 0 | 89–90 |
| 36 | Br | Cl | H | 0 | 139–142 |
| 37 | Br | H | CH3 | 0 | 163–165 |
| 38 | Br | CF3 | H | 0 | 101–106 |
| 39 | Br | SCF3 | H | 0 | 1.5956 |
| 40 | Br | H | H | 1 | 86–88 |
| 41 | CH3 | H | H | 1 | 60–63 |
| 42 | CH3 | H | Cl | 0 | 132–136 |
| 43 | C2H5 | H | Cl | 0 | 93–96 |
| 44 | C2H5 | Cl | H | 0 | 44–46 |
| 45 | C2H5 | H | H | 0 | 87–89 |
| 46 | C2H5 | H | H | 1 | 73–74 |
| 47 | C2H5 | H | CH3 | 0 | 90–92 |

TABLE 1-continued $$\text{structure with C(=O)-NH(CH}_2)_n\text{-phenyl(Y,Z), pyridine-N, O-phenyl(X)}$$

| Compound No. | X | Y | Z | n | m.p., °C., or $n_D^{30}$ |
|---|---|---|---|---|---|
| 48 | C$_2$H$_5$ | CH$_3$ | H | 0 | 64–65 |

The compounds listed in the foregoing Table 1 were tested for herbicidal activity utilizing the following procedures.

A. Pre-emergence Herbicide Screening Test

Using an analytical balance, 20 milligrams of the compound to be tested was weighed out on a piece of glassine weighing paper. The paper and compound were placed in a 30-milliliter wide-mouth bottle and 3 milliliters of acetone containing 1% polyoxyethylene sorbitan monolaurate emulsifying agent was added to dissolve the compound. If the material was not soluble in acetone, another solvent such as water, alcohol or dimethylformamide (DMF) was used instead. When DMF was used, only 0.5 milliliters or less was used to dissolve the compound and then another solvent was used to make the volume up to 3 milliliters. The milliliter solution was sprayed uniformly on the soil contained in a small flat one day after planting weed seeds therein. A No. 152 DeVilbiss atomizer was used to apply the spray using compressed air at a pressure of 5 lb./sq. in. (0.35 KG/cm$^2$). The rate of application was 8 lb./acre (8.96 kg./ha.) and the spray volume was 143 gal./acre (1338 lit./ha.)

On the day preceding treatment, the flat was filled to a depth of 2 inches with loamy sand soil. Seeds of seven different weed species were planted in individual rows using one species per row across the width of the flat. The seeds were covered with soil so that they were planted at a depth of 0.5 inch. The seeds used were hairy crabgrass (*Digitaria sanguinalis*), green foxtail (*Setaria viridis*), watergrass (*Echinochloa crusgalli*), red oat (*Avena sativa*), redroot pigweed (*Amaranthus retroflexus*), Indian mustard (*Brassica juncea*) and curly dock (*Rumex crispus*). Ample seeds were planted to give about 20 to 50 seedlings per row after emergence depending on the size of the plants.

After treatment, the flats were placed in the greenhouse at a temperature of 70° to 85° F. (21.1° to 29.4° C.) and watered by sprinkling. Two weeks after treatment the degree of injury or control was determined by comparison with untreated check plants of the same age. The injury rating from 0 to 100% was recorded for each species as percent control with 0% representing no injury and 100% representing complete kill.

B. Post-emergence Herbicide Screening Test

Seeds of six plant species, including hairy crabgrass, watergrass, red oat, mustard, curly dock and pinto beans (*Phaseolus vulgaris*) were planted in flats. The flats were placed in the greenhouse at 70° to 85° F. (21.1° to 29.4° C.) and watered daily with a sprinkler. About 10 to 14 days after planting when the primary leaves of the bean plants were almost fully expanded and the first trifoliate leaves were just starting to form, the plants were sprayed. The spray was prepared by weighing out 20 milligrams of the test compound, dissolving it in 2.5 milliliters of acetone containing 1% polyoxyethylene sorbitan monolaurate emulsifying agent and then adding 2.5 milliliters of water. The solution was sprayed on the soliage using a No. 152 DeVilbiss atomizer at an air pressure of 5 lb./sq. inch (0.35 kg./cm$^3$). The spray concentration was 0.1% and the rate 8 lb./acre (8.96 kg./ha.). The spray volume was 238 gal./acre (2226 lit./ha.).

The results of these tests are given in the following Table 2, in terms of average control of all plant species in the particular test. Ratings are on a scale of 0 to 100 as compared to an untreated check plot, with 0 representing no control and 100, complete kill. The values for post-emergence control represent the average control for all six plant species in that test. For pre-emergence control, the values for Compounds 1–34 represent average control of seven plant species. The values for Compound 35–48 represent average control of six plant species as these compounds were not tested against crabgrass.

TABLE 2

| Compound No. | Pre-emergence Control | Post-emergence Control |
|---|---|---|
| 1 | 79 | 57 |
| 2 | 61 | 50 |
| 3 | 73 | 55 |
| 4 | 61 | 73 |
| 5 | 40 | 12 |
| 6 | 23 | 37 |
| 7 | 48 | 2 |
| 8 | 44 | 5 |
| 9 | 79 | 61 |
| 10 | 82 | 68 |
| 11 | 83 | 73 |
| 12 | 72 | 63 |
| 13 | 87 | 60 |
| 14 | 85 | 70 |
| 15 | 90 | 51 |
| 16 | 87 | 47 |
| 17 | 83 | 59 |
| 18 | 60 | 32 |
| 19 | 73 | 43 |
| 20 | 84 | 67 |
| 21 | 29 | 50 |
| 22 | 6 | 17 |
| 23 | 82 | 23 |
| 24 | 82 | 55 |
| 25 | 79 | 46 |
| 26 | 72 | 51 |
| 27 | 70 | 44 |
| 28 | 26 | 22 |
| 29 | 74 | 43 |
| 30 | 66 | 14 |
| 31 | 49 | 16 |
| 32 | 43 | 2 |
| 33 | 40 | 43 |
| 34 | 82 | 76 |
| 35 | 71 | 22 |
| 36 | 71 | 38 |
| 37 | 85 | 30 |
| 38 | 88 | 44 |
| 39 | 64 | 40 |
| 40 | 68 | 63 |
| 41 | 31 | 28 |
| 42 | 62 | 34 |
| 43 | 80 | 42 |
| 44 | 69 | 62 |
| 45 | 71 | 50 |
| 46 | 23 | 30 |
| 47 | 83 | 28 |

TABLE 2-continued

| Compound No. | Pre-emergence Control | Post-emergence Control |
|---|---|---|
| 48 | 70 | 54 |

C. Herbicidal Evaluation (lower rates)

Selected compounds were further evaluated for pre-emergence and, in some cases post-emergence herbicidal activity at rates of application ranging variously from ¼ to 2 lb./acre. The procedures utilized were similar to those in the 1 lb./acre evaluations, but for the most part the spray rate was 80 gallons/acre (748 lit./ha.) and different weeds were involved. The weeds utilized were: broadleaf weeds: annual morningglory (*Ipomoea purpurea*), cocklebur (*Xanthium pennsylvanicum*), jimsonweed (*Datura stramonium*) velvetleaf (*Alutilon theophrasti*), Indian mustard (*Brassica juncea*), black nightshade (*Solanum nigrum*), redroot pigweed (*Amaranthus retroflexus*); grasses: downy broome (*Bromus tectorum*), foxtail (*Setaria* spp.) annual ryegrass (*Lolium multifluorum*) (Compounds 37, 38, 43, 44 and 45 only); watergrass (*Echinochloa crusgalli*), and wild oats (*Avena fatua*). Also tested in this series was yellow nutsedge (*Cyperus esculentus*). The results of these tests are shown in the following Table 3, with averages of ratings given for broadleaves and grasses. None of the compounds tested gave control of the nutsedge at these rates.

TABLE 3

| Compound No. | Rate, lb./acre | Broadleaf Avg. | Grass Avg. |
|---|---|---|---|
| PRE-EMERGENCE | | | |
| 1 | ¼ | 15 | 4 |
|   | ½ | 24 | 17 |
|   | 1 | 57 | 32 |
| 3 | ¼ | 6 | 29 |
|   | ½ | 27 | 41 |
|   | 1 | 36 | 56 |
| 10 | ¼ | 0 | 12 |
|   | ½ | 18 | 21 |
|   | 1 | 31 | 39 |
| 11 | ¼ | 24 | 42 |
|   | ½ | 63 | 63 |
|   | 1 | 75 | 76 |
| 12 | ¼ | 4 | 0 |
|   | ½ | 10 | 4 |
|   | 1 | 31 | 6 |
| 13 | ¼ | 3 | 46 |
|   | ½ | 20 | 64 |
|   | 1 | 63 | 71 |
| 14 | ¼ | 4 | 49 |
|   | ½ | 28 | 64 |
|   | 1 | 54 | 68 |
| 15 | ¼ | 7 | 66 |
|   | ½ | 45 | 81 |
|   | 1 | 77 | 87 |
| 16 | ¼ | 13 | 49 |
|   | ½ | 44 | 66 |
|   | 1 | 66 | 76 |
| 17 | ¼ | 9 | 38 |
|   | ½ | 64 | 50 |
|   | 1 | 74 | 56 |
| 23 | ¼ | 21 | 30 |
|   | ½ | 41 | 44 |
|   | 1 | 51 | 52 |
| 24 | ¼ | 11 | 22 |
|   | ½ | 34 | 26 |
|   | 1 | 51 | 56 |
| 25 | ¼ | 18 | 17 |
|   | ½ | 31 | 17 |
|   | 1 | 40 | 41 |
| 26 | ¼ | 13 | 17 |
|   | ½ | 27 | 23 |
|   | 1 | 34 | 40 |
| 27 | ¼ | 0 | — |
|   | ½ | 14 | — |
|   | 1 | 33 | — |
| 36 | ½ | 18 | 20 |
|   | 1 | 27 | 35 |
|   | 2 | 40 | 40 |
| 37 | 1 | 21 | 27 |
|   | 2 | 30 | 32 |
| 38 | ½ | 7 | 7 |
|   | 1 | 13 | 15 |
|   | 2 | 21 | 25 |
| 43 | ½ | 11 | 33 |
|   | 1 | 39 | 42 |
| 44 | ½ | 0 | 13 |
|   | 1 | 0 | 37 |
| 45 | ½ | 0 | 30 |
|   | 1 | 0 | 38 |
| 47 | ¼ | 14 | 22 |
|   | ½ | 20 | 61 |
|   | 1 | 23 | 74 |
| POST-EMERGENCE | | | |
| 3 | ¼ | 24 | 5 |
|   | ½ | 37 | 10 |
|   | 1 | 53 | 22 |
| 10 | ¼ | 25 | — |
|   | ½ | 48 | — |
|   | 1 | 62 | — |
| 11 | ¼ | 60 | 14 |
|   | ½ | 72 | 20 |
|   | 1 | 79 | 42 |
| 12 | ¼ | 46 | — |
|   | ½ | 57 | — |
|   | 1 | 72 | — |
| 14 | ¼ | 71 | — |
|   | ½ | 86 | — |
|   | 1 | 86 | — |

D. Herbicidal evaluation—Crops

Flats were filled with sandy loam soil containing the fungicide used in the two-pound tests and 17-17-17 fertilizer. The soil was leveled and a row marker used to impress seven rows across the width of the flat. Six to 60 seeds of each of the following crops were planted in one row apiece: field corn (*Zea mays*), cotton (*Gossypium herbaceum*), soybeans (*Glycine max*), rice (*Oryza sativa*), wheat (*Priticum aestivum*), and milo (*Sorghum vulgare*). The flats were placed in a greenhouse at 70°–85° F. (21.1°–29.4° C.) and watered by sprinkling.

Solutions of the test compounds were made by weighing out 300 milligrams of the compound into a bottle, dissolving it in 50 milliliters of acetone containing 1% polyoxyethylene sorbitan monolaurate emulsifying agent and diluting the solution to an appropriate concentration with water. If necessary, additional solvents were used in place of some of the acetone to dissolve the compound.

One day after planting, the flats were sprayed with test solutions of the compounds applied at rates of 1.0 and/or 2.0 pounds active ingredient per acre (1.12 and/or 2/24 kg./ha.) at a spray rate of 80 gallons of solution per acre (748 lit./ha.). The flats were returned to the greenhouse after spraying and watered daily by sprinkling. Three weeks after treatment, the degree of crop injury was estimated and recorded as percentage control compared to the growth of the same crop in an untreated check flat of the same age. In the case of compounds 36–38 and 43–47 the crops were planted in the same flats as the weeds described in evaluation C above.

TABLE 4

| Compound No. | Rate, lb./acre | Soybeans | Rice | Cotton | Corn | Milo | Wheat |
|---|---|---|---|---|---|---|---|
| PRE-EMERGENCE | | | | | | | |
| 1 | 2 | 0 | 0 | 0 | 0 | 0 | 0 |
| 3 | 2 | 5 | 0 | 0 | 0 | 5 | 0 |
| 10 | 2 | 50 | 0 | 40 | 0 | 0 | 0 |
| 11 | 1 | 20 | 0 | 30 | 20 | 0 | 0 |
|  | 2 | 60 | 0 | 40 | 30 | 10 | 0 |
| 12 | 2 | 10 | 0 | 10 | 0 | 0 | 0 |
| 13 | 1 | 10 | 0 | 40 | 10 | 40 | 0 |
|  | 2 | 10 | 10 | 60 | 20 | 70 | 0 |
| 14 | 1 | 0 | 0 | 40 | 0 | 10 | 0 |
|  | 2 | 20 | 0 | 60 | 10 | 20 | 0 |
| 15 | 1 | 40 | 50 | 40 | 80 | 80 | 0 |
|  | 2 | 60 | 80 | 60 | 85 | 98 | 20 |
| 16 | 1 | 0 | 20 | 40 | 40 | 0 | 0 |
|  | 2 | 10 | 40 | 60 | 60 | 10 | 0 |
| 17 | 2 | 30 | 40 | 30 | 75 | 30 | 0 |
| 23 | 1 | 0 | 20 | 0 | 0 | 0 | 0 |
|  | 2 | 10 | 10 | 60 | 50 | 0 | 0 |
| 24 | 1 | 10 | 0 | 0 | 40 | 20 | 0 |
|  | 2 | 10 | 50 | 0 | 65 | 50 | 0 |
| 25 | 2 | 0 | 0 | 10 | 30 | 0 | 0 |
| 26 | 2 | 0 | 10 | 60 | 0 | 0 | 0 |
| 27 | 2 | 0 | 10 | 20 | 0 | 0 | 0 |
| 29 | 2 | 0 | 0 | 10 | 0 | 0 | 0 |
| 36 | 1 | 0 | 0 | 10 | 0 | 0 | 0 |
|  | 2 | 0 | 10 | 0 | 0 | 10 | 0 |
| 37 | 1 | 0 | 0 | 0 | 0 | 0 | 0 |
|  | 2 | 10 | 0 | 30 | 0 | 0 | 0 |
| 38 | 1 | 0 | 0 | 10 | 0 | 0 | 0 |
|  | 2 | 10 | 0 | 10 | 0 | 0 | 0 |
| 43 | 1 | 0 | 0 | 10 | 0 | 10 | 0 |
| 44 | 1 | 0 | 0 | 0 | 0 | 10 | 0 |
| 45 | 1 | 0 | 0 | 0 | 20 | 10 | 0 |
| 47 | 1 | 0 | 0 | 0 | 0 | 20 | 20 |

As can be seen from the data in Tables 2-4, various compounds in this series show differing levels and types of activity. In the 8-lb. tests, some compounds produced good control as both pre-emergence and post-emergence herbicides; others showed best results in the pre-emergence tests. The activity of the compounds varied in many cases with respect to the weeds which were controlled. In some cases, compounds tested produced relatively low average values but were rather effective in controlling individual weed species. In general, little or no control of red oats, either in the pre- or post-emergence evaluation was observed at the 8 lb./acre rate. Nevertheless, with one exception (Compound 28), all the compounds in Table 1 produced control of 80% or better of at least one plant in these tests. Even compound 28 controlled pinto bean to a 60% extent.

In the 2 lb./acre tests, which generally involved different plant species than those at 8 lb., the activity of the compound was often quite substantial, even at levels as low as ½ lb./acre, in some cases.

Tests against crops (Table 4) show that many compounds may be additionally usable as selective herbicides. None of the compounds tested produced adverse effects on wheat at levels up to 2 lb./acre. Those compounds which show good weed control at levels of 2 lb./acre and less appear suitable for selectively controlling those weeds, and perhaps others not tested, in a wheat crop. Similarly, many of the compounds tested did not produce adverse effects on other crops, particularly corn and rice, and in a number of cases, soybeans and milo, and could be considered for selective control of weeds in the presence of these crops.

Even those compounds which produced crop damage or showed less activity at lower rates of application could be useful as broader spectrum herbicides, for instance for clearing roadbeds, highway median strips, building lots, vacant land and clearance of cropland prior to planting.

In general, those compounds in which X is halogen (particularly chloro) or trifluoromethyl and either Y or Z (or both) is hydrogen, appear to be the most active overall.

In practice, a pure compound can be used as a herbicide. However, in general, the compounds are first formulated with one or more inert carriers or diluents suitable for herbicidal use before being applied.

The compositions or formulations, including one or more compounds described herein, may take and be used in any one of a number of solid or liquid forms. Examples of solid forms are dusts, granules, tablets, powders and the like. Examples of liquid forms are emulsions, solutions, suspensions, emulsifiable concentrates and pastes. Such compositions may contain, in addition to the active compound or compounds, various carriers or diluents; surface active agents (wetting agents, dispersing agents and/or emulsifying agents); solvents (water or organic solvents such as aromatic solvents or chlorinated aliphatic solvents); adhesives; thickeners, binders; anti-foaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and alumino-silicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixtures, for example, by atomization, onto an absorptive granulated inert material, such as silica. Adhesives may be utilized to assist in the incorporation of the compound onto the solid.

Wettable powders and pastes are obtained by mixing and grinding an active compound with one or more dispersing agents and/or solid carriers or diluents. Also included are wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are also added.

In general, compositions may contain from 0.1 to 95% of the active compound, more preferably from 0.5 to 90%. Some typical compositions will contain an active compound as follows: wettable powders —20 to 90% active compound; oil suspensions, emulsions, solutions and emulsifiable concentrates —5 to 90% active compound; aqueous suspensions —10 to 50% active compound; dusts and powders —1 to 25% active compound; granules and pellets —1 to 20% active compound.

The rate of application of the active compound to a locus to be controlled will depend on the nature of the compound, the seeds and plants to be controlled and whether or not selective control is sought, and may vary from about 0.05 to about 50 pounds per acre (about 0.06 to about 56 kg./ha.).

In addition to the active compound and the various agents utilized in preparing compositions and formulations mentioned above, such compositions may also contain one or more other active compounds of the type mentioned herein as well as other active pesticidal agents, such as herbicides, fungicides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds in a herbicidally effective amount may be applied to the plant or locus to be controlled in any conventional manner. Thus, powders and various liquid compositions containing the active compound can be applied by the use of powder dusters, boom and hand sprayers and spray dusters, or applied from airplanes as dusts or sprays. When applied in the latter method, they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

Compositions applied to the surface of the soil can be distributed below the surface of the soil by conventional means such as discing or mixing operations.

What is claimed is:

1. A compound having the formula

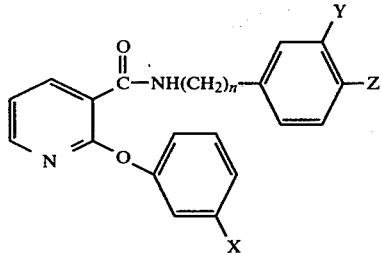

in which n is 0 or 1; X is halogen, $C_1$–$C_3$ alkyl, trifluoromethyl or carboethoxy; Y and Z are independently hydrogen, lower alkyl, halo-lower alkyl, thio(halo-lower alkyl), nitro, cyano or halogen; provided that:
   if X is carboethoxy, Z is halogen and Y is hydrogen or halogen; and
   if Y and Z are both halogen, X is halogen, trifluoromethyl or carboethoxy.

2. A compound according to claim 1 in which X is chloro, bromo, methyl, ethyl or trifluoromethyl.

3. A compound according to claim 2 in which one of Y and Z is hydrogen.

4. A compound according to claim 2 in which one of Y and Z is hydrogen and the other is chloro, bromo, methyl, cyano or trifluoromethyl.

5. A compound according to claim 2 in which Y and Z are both hydrogen and n is 0.

6. A compound according to claim 3 in which X is chloro.

7. A compound according to claim 3 in which X is trifluoromethyl.

8. A compound according to claim 1 in which n is 0, X and Y are trifluoromethyl and Z is hydrogen.

9. A compound according to claim 1 in which n is 0, X is trifluoromethyl, Y is trifluoromethylthio and Z is hydrogen.

10. A compound according to claim 1 in which n is 0, X is trifluoromethyl, Y is nitro and Z is hydrogen.

11. A compound according to claim 1 in which n is 0, X and Z are chloro and Y is trifluoromethyl.

12. A compound according to claim 1 in which n is 0, and X, Y and Z are each chloro.

13. A compound according to claim 1 in which n is 0, X is chloro, Y is trifluoromethylthio and Z is hydrogen.

14. A compound according to claim 1 in which n is 0, X is chloro, Y is nitro and Z is hydrogen.

15. A compound according to claim 1 in which n is 0, X is chloro and Y and Z are methyl.

16. A compound according to claim 1 in which n is 0, X and Y are trifluoromethyl and Z is chloro.

17. A compound according to claim 1 in which n is 0, X is trifluoromethyl and Y and Z are methyl.

18. A compound according to claim 1 in which n is 0, X is trifluoromethyl, Y is hydrogen and Z is chloro.

19. A compound according to claim 1 in which n is 0, X is trifluoromethyl and Y and Z are chloro.

20. A compound according to claim 1 in which n is 0, X is trifluoromethyl, Y is chloro and Z is hydrogen.

21. A compound according to claim 1 in which n is 0, X is trifluoromethyl, Y is hydrogen and Z is bromo.

22. A compound according to claim 1 in which n is 0, X is trifluoromethyl and Y and Z are hydrogen.

23. A compound according to claim 1 in which n is 0, X is trifluoromethyl, Y is hydrogen and Z is methyl.

24. A compound according to claim 1 in which n is 0, X is trifluoromethyl, Y is hydrogen and Z is cyano.

25. A compound according to claim 1 in which n is 0, X is trifluoromethyl, Y is hydrogen and Z is nitro.

26. A compound according to claim 1 in which n is 0, X is trifluoromethyl, Y is methyl and Z is hydrogen.

27. A compound according to claim 1 in which n is 0, X is carboethoxy, Y is hydrogen and Z is chloro.

28. A compound according to claim 1 in which n is 0, X is carboethoxy and Y and Z are chloro.

29. A compound according to claim 1 in which n is 0, X and Z are chloro and Y is hydrogen.

30. A compound according to claim 1 in which n is 0, X is chloro and Y and Z are hydrogen.

31. A compound according to claim 1 in which n is 0, X is chloro, Y is hydrogen and Z is methyl.

32. A compound according to claim 1 in which n is 0, X and Y are chloro and Z is hydrogen.

33. A compound according to claim 1 in which n is 0, X is chloro, Y is trifluoromethyl and Z is hydrogen.

34. A compound according to claim 1 in which n is 0, X is chloro, Y is hydrogen and Z is bromo.

35. A compound according to claim 1 in which n is 0, X is methyl and Y and Z are hydrogen.

36. A compound according to claim 1 in which n is 0, X is methyl, Y is chloro and Z is hydrogen.

37. A compound according to claim 1 in which n is 0, X and Z are methyl and Y is hydrogen.

38. A compound according to claim 1 in which n is 0, X is chloro, Y is methyl and Z is hydrogen.

39. A compound according to claim 1 in which n is 1, X is chloro and Y and Z are hydrogen.

40. A compound according to claim 1 in which n is 0, X is bromo, Y is chloro and Z is hydrogen.

41. A compound according to claim 1 in which n is 0, X is bromo, Y is hydrogen and Z is methyl.

42. A compound according to claim 1 in which n is 0, X is bromo, Y is trifluoromethyl and Z is hydrogen.

43. A compound according to claim 1 in which n is 0, X is bromo, Y is trifluoromethylthio and Z is hydrogen.

44. A compound according to claim 1 in which n is 1, X is bromo and Y and Z are hydrogen.

45. A compound according to claim 1 in which n is 1, X is methyl and Y and Z are hydrogen.

46. A compound according to claim 1 in which n is 0, X is methyl, Y is hydrogen and Z is chloro.

47. A compound according to claim 1 in which n is 0, X is ethyl, Y is hydrogen and Z is chloro.

48. A compound according to claim 1 in which n is 0, X is ethyl, Y is chloro and Z is hydrogen.

49. A compound according to claim 1 in which n is 0, X is ethyl and Y and Z are hydrogen.

50. A compound according to claim 1 in which n is 1, X is ethyl and Y and Z are hydrogen.

51. A compound according to claim 1 in which n is 0, X is ethyl, Y is hydrogen and Z is methyl.

52. A compound according to claim 1 in which n is 0, X is ethyl, Y is methyl and Z is hydrogen.

* * * * *